United States Patent [19]

Huston

[11] Patent Number: 5,126,676

[45] Date of Patent: Jun. 30, 1992

[54] GAS AMPLIFIED IONIZATION DETECTOR FOR GAS CHROMATOGRAPHY

[75] Inventor: Gregg C. Huston, LaBelle, Pa.

[73] Assignee: The United States of America as represented by the United States Department of Energy, Washington, D.C.

[21] Appl. No.: 441,582

[22] Filed: Nov. 27, 1989

[51] Int. Cl.$^5$ .................................. G01N 27/62
[52] U.S. Cl. ........................... 324/464; 250/379
[58] Field of Search ........... 324/464, 459, 462, 470; 73/23.1; 250/379, 383

[56] References Cited

U.S. PATENT DOCUMENTS

| | | | |
|---|---|---|---|
| 3,087,113 | 4/1963 | Foster | 324/464 |
| 3,585,003 | 6/1971 | Scolnick | 250/379 |
| 3,676,682 | 7/1972 | Falk | 250/385.1 |
| 3,870,880 | 3/1975 | Lovelock | 250/379 |
| 4,028,617 | 6/1977 | Kamo et al. | 324/464 |
| 4,398,152 | 8/1983 | Leveson | 324/464 |
| 4,508,685 | 4/1985 | Sisti et al. | 324/420 |
| 4,587,429 | 5/1986 | Tomoda et al. | 250/375 |
| 4,769,548 | 9/1988 | Burtscher et al. | 324/464 |
| 4,837,440 | 6/1989 | Burtscher et al. | 250/329 |

FOREIGN PATENT DOCUMENTS

| | | | |
|---|---|---|---|
| 259257 | 8/1988 | Fed. Rep. of Germany | 324/464 |
| 972387 | 11/1982 | U.S.S.R. | 324/464 |
| 972388 | 11/1982 | U.S.S.R. | 324/464 |
| 1004873 | 3/1983 | U.S.S.R. | 324/464 |
| 1057840 | 11/1983 | U.S.S.R. | 324/464 |

OTHER PUBLICATIONS

Industrial and Engineering Chemistry, vol. 52, #11; pp. 61A-64A, Ionization Detectors for Gas Chromatography, Stirling et al, Nov. 1960.
Analytical Chemistry, vol. 33; #2; pp. 162-178, Ionization Methods for Analysis of Gases and Vapors, Lovelock Feb. 1960.

Primary Examiner—Kenneth A. Wieder
Assistant Examiner—Naura K. Regan
Attorney, Agent, or Firm—David E. Breeden; Stephen D. Hamel; William R. Moser

[57] ABSTRACT

A gas-amplified ionization detector for gas chromatrography which possesses increased sensitivity and a very fast response time. Solutes eluding from a gas chromatographic column are ionized by UV photoionization of matter eluting therefrom. The detector is capable of generating easily measured voltage signals by gas amplification/multiplication of electron products resulting from the UV photoionization of at least a portion of each solute passing through the detector.

6 Claims, 3 Drawing Sheets

GAS AMPLIFIED IONIZATION DETECTOR FOR GAS CHROMATOGRAPHY

BACKGROUND OF THE INVENTION

This invention relates generally to gas chromatographic detectors, and more particularly to gas chromatographic detectors using ionization of a sample solute with concurrent amplification of electron products via gas amplification.

The present invention is applicable to analytical chemistry in the subdisciplines of high speed analysis of complex organic mixtures and trace analysis. With regard to complex mixture analysis, there currently exists technology suitable to the production of gas chromatographic capillary columns possessing extraordinary separating capability. However, gas chromatographic detector technology is found to be currently inadequate and is a principal factor that prevents full utilization of capillary column manufacturing technology. More specifically, gas chromatographic detector sensitivity and response time limitations prevent the full utilization of capillary column manufacturing technology. The detector of the present invention was designed to overcome this barrier.

SUMMARY OF THE INVENTION

It is thus an object of the present invention to provide a new type of gas chromatographic detector which possesses a very high degree of sensitivity and very rapid response time through the coupling of ionization of a chromatographical solute with gas amplification.

It is a further object of the present invention to provide a gas chromatographic detector which possesses a degree of variable selectivity based on the differences in ionization potential of compounds eluting from the chromatographic sample column.

The objects of the present invention are fulfilled by providing a system for detecting solutes eluting from a chromatographic column comprising a cathode electrode, a thin wire anode electrode located in a spaced relationship with the cathode electrode, a high voltage supply connected between the anode and cathode electrodes to produce an electric field gradient therebetweeen, and insulative housing enclosing the space between the anode and cathode electrodes to form a detection chamber, an ionization source for providing selected ionization of at least a portion of each solute eluted into said chamber, means for introducing the solutes into the chamber including a carrier gas capable of providing gas amplification of each ionization event due to the electric field gradient applied between the anode and cathode electrodes, and a detection means coupled to the anode electrode for detecting each ionization event as a voltage pulse produced through the collection of electrons at said anode electrode so that the number of ionization events detected per unit time is indicative of the concentration of the solute passing through the detection chamber.

Further scope of applicability of the present invention will become apparent from the detailed description given hereinafter. However, it should be understood that the description and specific examples, while indicating preferred embodiments of the invention, are given by way of illustration only since various changes and modifications within the spirit and scope of the invention will become apparent to those skilled in the art from this description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENT

Figure 1:
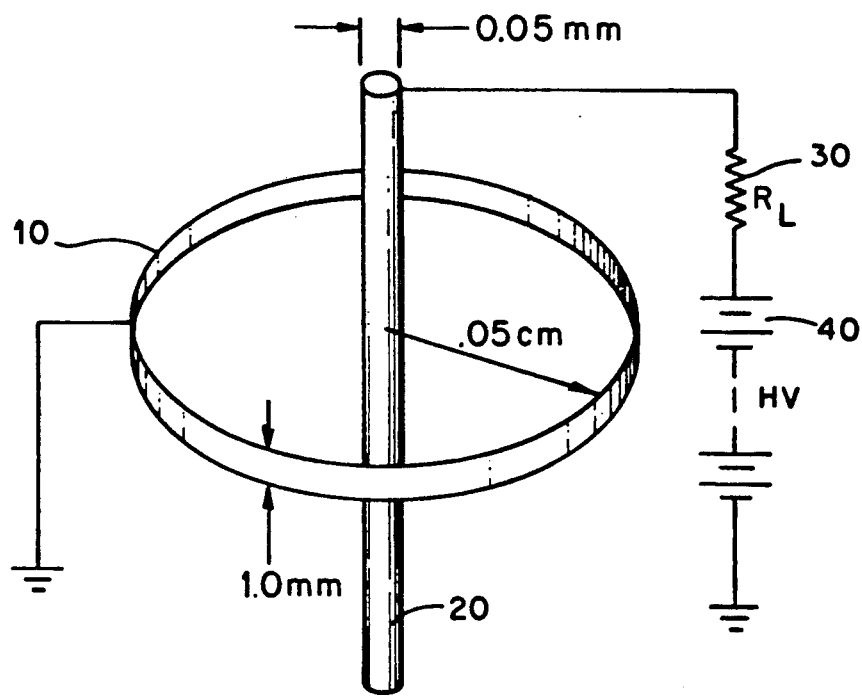
FIG. 1 is a schematic diagram of the electrode arrangement of a gas-amplified photoionization detector according to the present invention.

FIG. 1 is a schematic diagram illustrating the basic electrode arrangement of a gas-amplified photoionization detector (GAPID) of the present invention.

A thin wire anode electrode 20 is located at the central axis of a cylindrical cathode 10. The cathode 10 and the anode 20 are preferably formed of gold. A high voltage source 40 is connected to the anode electrode 20 via a load resistor 30, while the cathode electrode 10 is grounded, to create an electric field E between the anode and cathode electrodes. The amplification of an electron produced by photoionization is achieved by a process known as gas amplification or multiplication. When an electron is produced within an electric field of sufficient strength, the electron will accelerate toward the anode, impinging upon surrounding gas molecules to produce n ion pairs. The magnitude of n depends critically on the E/P ratio where P is the pressure of the gas. As electrons are collected at the anode, a change in voltage at the load resistor occurs which is detected as a time dependent voltage signal or voltage pulse. It will be understood that although photoionization is illustrated here as the solute ionizing means, various other known means for producing selected ionization may be employed.

Because of the electrode geometry, the ratio E/P is greater near anode 20, and therefore amplification is greatest in this vicinity. Since the mobility of free electrons is greater than the mobility of positive ions, some of the electrons formed during the amplification process are collected at the anode quicker than positive ions that migrate toward the cathode, thereby leaving a positive space charge between the anode and cathode. As a consequence, the remaining electrons are collected more slowly. Thus, the shape of the voltage pulse detected across the load resistor 30 is related to the positive ion drift time $t_+$. Ion drift times in the gas amplification voltage region should be fast enough to allow the monitoring of fast ion production rates. As a result, individual ionization events as voltage pulses can be monitored, with the count rate of the pulses being proportional to the concentration of solute being measured. Monitoring is accomplished using an electronic arrangement consisting of a charge sensitive preamplifier, main shaping amplifier, a single channel analyzer, and a multichannel analyzer (MCA) operated in a single channel scaling mode. The actual chromatogram is recorded on the MCA.

Sufficient voltage V should be supplied across the electrodes 10 and 20 of FIG. 1 to produce gas-amplification should an ionizing event occur within the electric field E between the electrodes 10 and 20. the magnitude of E at any distance r from the center of the anode is given by;

$$E_{(r)} = \frac{V}{r \ln(b/a)}$$

Where:
E$_{(r)}$ = electric field at a distance r
V = applied voltage
b = cathode radius
a = anode radius
r = distance from anode center The gas amplification that can be achieved for any given applied voltage can be calculated from the expression:

$$\ln A = \frac{V}{\ln(b/a)} \frac{\ln 2}{\Delta V} \left[ \ln \left( \frac{V}{Pa\ln(b/a)} \right) - \ln K \right]$$

Where:
A = gain
P = gas pressure
ΔV = potential difference through which an electron moves between successive ionizing events
K = minimum value of E/P below which amplification cannot occur.

Known values of ΔV and K for P−10 carrier gas (10% methane 90% argon) were used to calculate a value for the anode radius necessary for an amplification range of $10^4$ to $10^9$ over an applied high voltage range of 1800 to 2700 V. A cathode radius b was selected to be 0.5 cm after considering the positive ion drift time and its effect on the detector's ability to accurately measure at fast counting rates. The positive ion drift time will affect the detector's resolving ability to detect closely timed ionization events in situations in which the applied voltage is sufficiently large so that a positive space charge will develop initially surrounding the anode to reduce the value of E below a value necessary for sufficient gas amplification and the net charge produced will be too small to be detected. The positive ion space charge will drift towards the cathode and diffuse to restore E to a value great enough for sufficient multiplication to reoccur after another ionization event takes place. The period of sufficient restoration of E is known as the detector's dead time T during which no ionization events can be monitored.

The distance that the anode and cathode should be separated to enhance the detector's ability to resolve closely timed ionization events can be calculated in terms of detector dead time by setting a percentage limit on the number of ionization events lost due to the dead time. Using such limits, it is possible to calculate a radius for an acceptable level of detector sensitivity. The dead time T governs the useful linear detection range of the detector since the larger T becomes, the smaller the amount of material entering the detector must become in order to keep count losses at an acceptable level. T can be made much smaller than $t_+$.

The magnitude of the voltage pulse produced from a single ionization event is given by:

$$V = Q/C = eA/C.$$

Where:
e = electronic charge
C = capacitance of the detector and preamplifier
Q = total charge collected on the anode.

It has been experimentally determined that for an applied voltage great enough to produce a gas amplification of $10^7$ (approximately 2300 volts), the voltage pulse produced from a single ionization event in the detector would have an amplitude of several volts. As a long pulse width is not conducive to fast counting rates, pulse shaping circuits are used in which pulse width reduction is easily accomplished by passing the detector output through pulse shaping circuits (contained within the preamplifier and main shaping amplifier).

Figure 2:
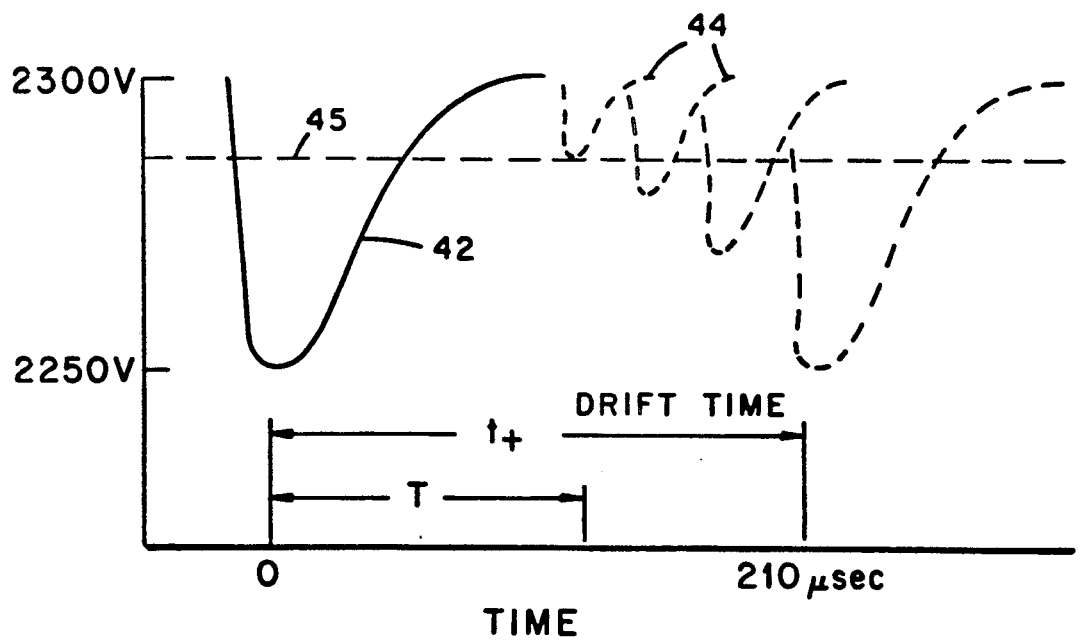
FIG. 2 is a graph illustrating an individual ionization event detected as a voltage pulse.

FIG. 2 illustrates an example of a shaped voltage pulse with the solid curve 42 being the shape of a processed voltage pulse and the broken curves 44 representing voltage pulses generated if a second ionization event occurred within a short time of the initial event. Even though the shaped voltage pulse has decayed back to the starting voltage, a positive space charge will still exist inside the detector at this time so that another voltage pulse cannot form until the positive space charge has dissipated to an extent where the effective voltage is great enough for sufficient gas amplification to occur. After the voltage has recovered to such a value, a second ionization event will trigger a discharge and another voltage pulse will be produced. However, the amplitude of the second pulse will be smaller than the amplitude of the first pulse if the second event occurs within a time period less than $t_+$. Whether a reduced amplitude pulse will be registered by the counter depends on the minimum pulse height required by the counter which is controlled by a single channel analyzer. A typical single channel analyzer setting, as generally shown at line 45, is about 0.5 volt. Therefore, a positive space charge remaining in the detector would have to dissipate only to an extent where the gas gain A is sufficient to produce a 0.5 voltage pulse from a second ionization event. Therefore, if the time required for the positive space charge to dissipate to such an extent that gas amplification is high enough to produce a 0.5 volt voltage pulse from a single ionization event is determined, the maximum count rate of the detector could also be determined. The maximum count rate has been calculated to be between 381,000 and 385,000 counts per second according to extreme models. For typical background radiation count rates of 10 counts per second, the GAPID will have a linear dynamic range of five orders of magnitude.

Since the gas amplification detector produces a very large signal in the form of voltage pulses, the conventional electronic noise does not significantly contribute to the signal-to-noise ratio of the detector. Instead, sources of background radiation must be considered as the principal noise producing contributors. To limit the contribution of background radiation noise to an insignificant amount, gold is a preferred material to be used for the anode and cathode since it does not contain any naturally occurring radioactive isotopes.

Figure 3:
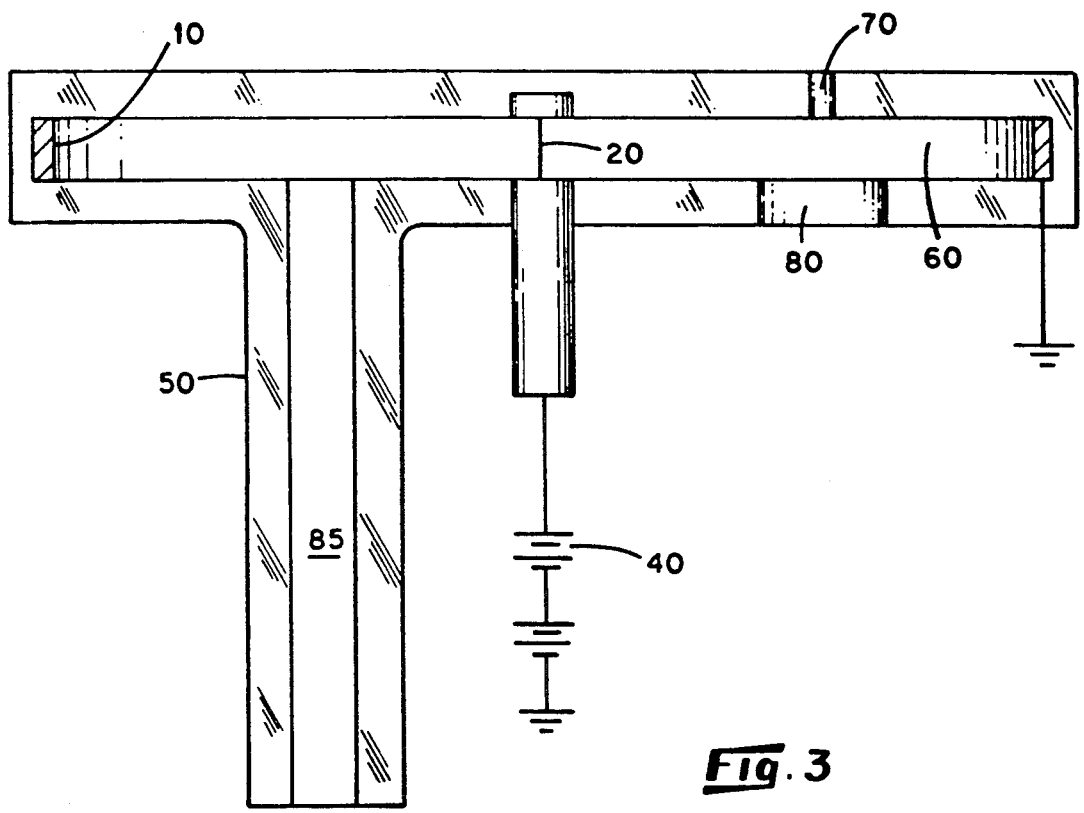
FIG. 3 is a cross sectional view of the electrode arrangement of the gas amplification detector within an insulative housing jacket.

FIG. 3 shows a cross sectional view of the electrode assembly in which a housing 50 is constructed of borosilicate glass to insulate the electrodes 10 and 20. Borosilicate glass does not transmit far UV light and thus will assist in preventing photoelectronic emission from electrode surfaces by stray photons.

The UV light should enter the detector volume 60 perpendicular to the plane of the electric field to prevent direct photoionization of the anode and cathode materials. A UV light entry window 70 is provided through which the UV light enters the detector volume. A light trap 80 is provided opposite to the light entry port to remove practically all of the unabsorbed UV radiation. A line 85 is used for conveying the make-up carrier gas into the detector volume 60 of housing 50.

Figure 4:
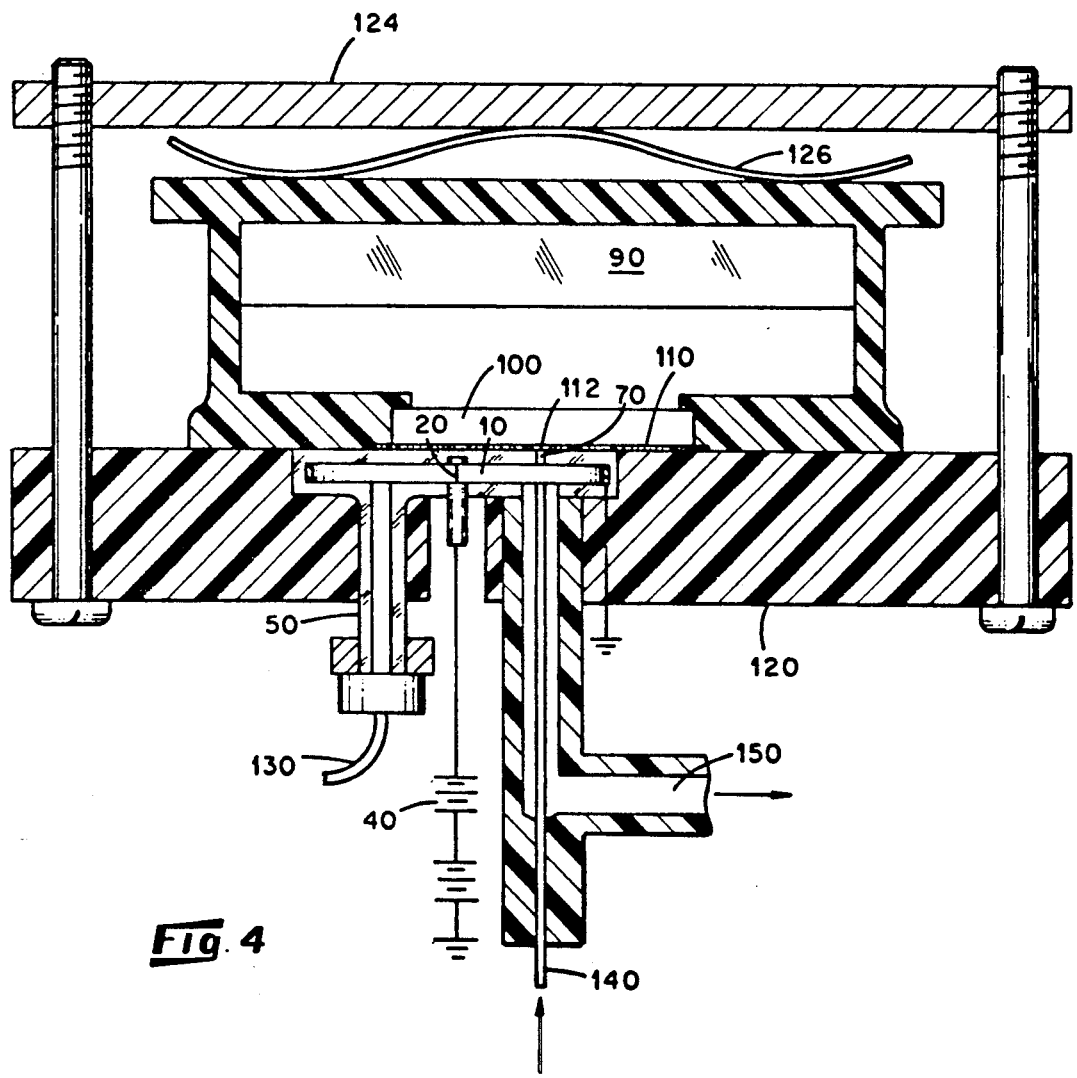
FIG. 4 is a cross sectional view of the gas amplification detector with associated UV light source, inlet and outlet ports, and associated housing.

FIG. 4 illustrates a complete cross sectional view of the gas amplification detector. A UV light source, such as a UV light bulb shown at 90, is provided above a magnesium fluoride window 100 and a vespel disc 110 which contains a hole 112 that can be varied in size to change the UV light intensity entering the detector volume. The UV light emits primarily at the Lyman alpha line wavelength. The entire assembly of FIG. 3 is inserted into an insulative casing 120. A simple clamping arrangement 124 with a retaining washer 126 is used to hold the UV light source in proper registry with the detector volume 86. A carrier gas make-up port 130 is provided for the injection of the amplification gas, a sample inlet port 140 formed of a capillary of fused silica is provided for the injection of a fluid sample to be tested, and a gas exit port or vent 150 is provided to evacuate the detector volume.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A system for detecting solutes eluting from a chromatographic column by gas-amplified ionization, comprising:

a cathode electrode;

an anode electrode formed of a thin wire and located in a spaced relationship with said cathode electrode to provide an electric field gradient in a detection region formed therebetween upon application of a high voltage between said anode and cathode electrodes sufficient to produce gas-amplified detection of an ionization event in said detection region;

means for providing said high voltage between said anode and cathode electrodes;

an insulative housing enclosing said detection region;

means for transporting solutes to be detected through said detection region in a carrier gas capable of supporting gas amplification;

photoionization means for providing specific ionization of at least a portion of each of said solutes as it passes through said detection region; and detection means coupled to said anode electrode for detecting each ionization event as a voltage pulse produced through the collection of electrons at said anode electrode so that the number of ionization events detected per unit time is indicative of the concentration of the solute passing through said detection region.

2. A system as defined in claim 1 wherein said photoionization means includes a UV light source means for providing an amount of UV light into said chamber sufficient to produce at least partial photoionization of said solute passing through said detection region.

3. A system as defined in claim 2, wherein said insulative housing is formed of borosilicate glass.

4. A system as defined in claim 2, wherein said cathode and anode electrodes are formed of gold.

5. A system as defined in claim 2 wherein said means for transporting solutes includes a gas inlet and a gas exhaust port formed in said housing in fluid communication with said detection region through which said carrier gas passes into and out of said detection region and a capillary inlet port disposed for introduction of said solutes into said detection region.

6. A system as defined in claim 5, wherein said UV light source means includes a UV light source, a transparent window formed in said housing for introducing light from said UV light source into said housing along a path perpendicular to said electric field gradient and onto said solute as it exits said capillary port and a light trapping means disposed in the wall of said housing opposite said window for removing unabsorbed UV light from said housing.

* * * * *